(12) United States Patent
Gut et al.

(10) Patent No.: US 6,503,710 B2
(45) Date of Patent: Jan. 7, 2003

(54) MUTATION ANALYSIS USING MASS SPECTROMETRY

(76) Inventors: Ivo Glynne Gut, 18 rue du Moulin Vert, 75014 Paris (FR); Kurt Berlin, Marienkaferweg 4, 14532 Stahnsdorf (DE); Doris Lechner, 73 avenue du General Michel Bizot, 75012 Paris (FR); Hans Lehrach, Terrassenstrasse 31, 14129 Berlin (DE)

( * ) Notice: Subject to any disclaimer, the term of this patent is extended or adjusted under 35 U.S.C. 154(b) by 0 days.

(21) Appl. No.: 09/321,005

(22) Filed: May 27, 1999

(65) Prior Publication Data

US 2002/0162622 A1 Nov. 7, 2002

(30) Foreign Application Priority Data

May 29, 1998 (DE) .......................................... 198 24 280

(51) Int. Cl.[7] ........................... C07H 21/04; C12Q 1/68
(52) U.S. Cl. ................... 435/6; 435/91.1; 536/25.3; 536/25.4; 436/173; 436/175
(58) Field of Search ................... 435/6, 91.1; 536/25.3, 536/25.4; 436/173, 175

(56) References Cited

U.S. PATENT DOCUMENTS 5,547,835 A * 8/1996 Koster ........................... 435/6

FOREIGN PATENT DOCUMENTS

| GB | 2325002 A | 11/1998 | |
|----|-----------|---------|---|
| GB | 2339279 A | 1/2000 | |
| WO | WO 96/27681 A1 | 9/1996 | |
| WO | WO 96/37630 | * 11/1996 | ............ C12Q/1/68 |
| WO | WO 97/47766 A1 | 12/1997 | |
| WO | WO 98/14616 A1 | 4/1998 | |
| WO | WO 99/14362 | 3/1999 | |

OTHER PUBLICATIONS

Bentzley et al "Oligonucleotide sequence and composition determined by MALDI" Analytical Chemistry, vol. 68, pp. 2141–2146, Jul. 1996.*

Nakanishi et al "Laser Desorption TOF MALDI of Transferrin precipitated with Antiserum: a unique simple method to identify molecular weight variants" Biological Mass Spectrometry, vol. 23, pp. 230–233, 1994.*

Ross et al "High level multiplex genotyping by MALDI–TOF mass spectrometry" Nature Biotechnology, vol. 16, pp. 1347–1351, Dec. 1998.*

Stratagen Catalog, 1988.*

Sauer et al "A novel procedure for efficient genotypin gof SNPS" Nucleic Acids Research, vol. 28, No. 5, pp. e13, 2000.*

Daniel P. Little et al.; Detection of RET proto–oncogene codon 634 mutations using mass spectrometry; J Mol Med (1997) 75: pp. 745–750.

Spitzer, et al., Inhibition of Deoxyribonucleases by Phosphorothioate Groups in Oligodeoxyribonucleotides, Nucleic Acids Research, 1988, vol. 16, (Abstract).

Schreiber, et al., Selective Protection of In Vitro Synthesized cDNA Against Nucleases by Incorporation of Phosphorothioate–analogues, Nucleic Acids Research, 1985, vol. 13, (Abstract).

* cited by examiner

*Primary Examiner*—Jeffrey Fredman
*Assistant Examiner*—Jeanine Goldberg

(57) ABSTRACT

The invention presents a method for examining genetic material (deoxyribonucleic acid, DNA) to detect the presence of pre-known mutations, especially single nucleotide polymorphisms (SNP), using mass spectrometry with ionization by matrix-assisted laser desorption (MALDI). The invention uses nucleoside triphosphates with modified sites for the method of primer extension in a duplicating, enzymatic reaction and at least partially removal of primers from the extension product, in combination with product neutralization by chemical treatment of the modified sites, so that the resulting DNA products can be, by using special matrix materials, preferredly ionized in an adduct-free form over other constituents in the reaction solution without any further cleaning. The method is particularly suitable for simultaneous identification of several mutations by multiplexing.

22 Claims, 5 Drawing Sheets pt = Phosphorothioate
p = Phosphate 4) 5'——— BptB-3'

5) 5'——— BpB-3'

SEQUENCE LISTING

<160> NUMBER OF SEQ ID NOS: 17

<210> SEQ ID NO 1
<211> LENGTH: 30
<212> TYPE: DNA
<213> ORGANISM: Artificial
<220> FEATURE:
<223> OTHER INFORMATION: Hypothetical Sequence for Exemplary Purposes

<400> SEQUENCE: 1
tcctgcatgg gcatgaaccg gaggcccatc          30

```
<210> SEQ ID NO 2
<211> LENGTH: 30
<212> TYPE: DNA
<213> ORGANISM: Artificial
<220> FEATURE:
<223> OTHER INFORMATION: Hypothetical Sequence for Exemplary Purposes

<400> SEQUENCE: 2
tcctgcatgg gcatgaaccg gagtcccatc                                         30

<210> SEQ ID NO 3
<211> LENGTH: 21
<212> TYPE: DNA
<213> ORGANISM: Artificial
<220> FEATURE:
<223> OTHER INFORMATION: Hypothetical Sequence for Exemplary Purposes

<400> SEQUENCE: 3
ctgcatgggc ggcatgaacc g                                                  21

<210> SEQ ID NO 4
<211> LENGTH: 25
<212> TYPE: DNA
<213> ORGANISM: Artificial
<220> FEATURE:
<223> OTHER INFORMATION: Hypothetical Sequence for Exemplary Purposes

<400> SEQUENCE: 4
agctactgat gctgtgcaga tactt                                              25

<210> SEQ ID NO 5
<211> LENGTH: 25
<212> TYPE: DNA
<213> ORGANISM: Artificial
<220> FEATURE:
<223> OTHER INFORMATION: Hypothetical Sequence for Exemplary Purposes

<400> SEQUENCE: 5
agctactgat gctgtgcaga cactt                                              25

<210> SEQ ID NO 6
<211> LENGTH: 17
<212> TYPE: DNA
<213> ORGANISM: Artificial
<220> FEATURE:
<223> OTHER INFORMATION: Hypothetical Sequence for Exemplary Purposes

<400> SEQUENCE: 6
agctactgat gctgtgc                                                       17

<210> SEQ ID NO 7
<211> LENGTH: 17
<212> TYPE: DNA
<213> ORGANISM: Artificial
<220> FEATURE:
<223> OTHER INFORMATION: Hypothetical Sequence for Exemplary Purposes

<400> SEQUENCE: 7
ggaacagctt tgaggtg                                                       17

<210> SEQ ID NO 8
<211> LENGTH: 27
<212> TYPE: DNA
<213> ORGANISM: Artificial
<220> FEATURE:
<223> OTHER INFORMATION: Hypothetical Sequence for Exemplary Purposes
```

```
<400> SEQUENCE: 8
ggaacagctt tgaggtgcgt gtttgtg                                           27

<210> SEQ ID NO 9
<211> LENGTH: 27
<212> TYPE: DNA
<213> ORGANISM: Artificial
<220> FEATURE:
<223> OTHER INFORMATION: Hypothetical Sequence for Exemplary Purposes

<400> SEQUENCE: 9
ggaacagctt tgaggtgcat gtttgtg                                           27

<210> SEQ ID NO 10
<211> LENGTH: 17
<212> TYPE: DNA
<213> ORGANISM: Artificial
<220> FEATURE:
<223> OTHER INFORMATION: Hypothetical Sequence for Exemplary Purposes

<400> SEQUENCE: 10
ggaacagctt tgaggtg                                                      17

<210> SEQ ID NO 11
<211> LENGTH: 30
<212> TYPE: DNA
<213> ORGANISM: Artificial
<220> FEATURE:
<223> OTHER INFORMATION: Hypothetical Sequence for Exemplary Purposes

<400> SEQUENCE: 11
gctgacattg aaatatggcg ccaagcatgt                                        30

<210> SEQ ID NO 12
<211> LENGTH: 30
<212> TYPE: DNA
<213> ORGANISM: Artificial
<220> FEATURE:
<223> OTHER INFORMATION: Hypothetical Sequence for Exemplary Purposes

<400> SEQUENCE: 12
gctgacattg aaatatggcg tcaagcatgt                                        30

<210> SEQ ID NO 13
<211> LENGTH: 17
<212> TYPE: DNA
<213> ORGANISM: Artificial
<220> FEATURE:
<223> OTHER INFORMATION: Hypothetical Sequence for Exemplary Purposes

<400> SEQUENCE: 13
gctgacattg aaatatg                                                      17

<210> SEQ ID NO 14
<211> LENGTH: 11
<212> TYPE: DNA
<213> ORGANISM: Artificial
<220> FEATURE:
<223> OTHER INFORMATION: Hypothetical Sequence for Exemplary Purposes

<400> SEQUENCE: 14
gcgccaagca t                                                            11

<210> SEQ ID NO 15
<211> LENGTH: 27
```

-continued

```
<212> TYPE: DNA
<213> ORGANISM: Artificial
<220> FEATURE:
<223> OTHER INFORMATION: Hypothetical Sequence for Exemplary Purposes

<400> SEQUENCE: 15
attgaaatat ggcgccaagc atgtgat                                27

<210> SEQ ID NO 16
<211> LENGTH: 27
<212> TYPE: DNA
<213> ORGANISM: Artificial
<220> FEATURE:
<223> OTHER INFORMATION: Hypothetical Sequence for Exemplary Purposes

<400> SEQUENCE: 16
attgaaatat ggcgccaagc atttgat                                27

<210> SEQ ID NO 17
<211> LENGTH: 19
<212> TYPE: DNA
<213> ORGANISM: Artificial
<220> FEATURE:
<223> OTHER INFORMATION: Hypothetical Sequence for Exemplary Purposes

<400> SEQUENCE: 17
attgaaatat ggcgccaag                                         19
```

MUTATION ANALYSIS USING MASS SPECTROMETRY

FIELD OF INVENTION

The invention presents a method for examining genetic material (desoxyribonucleic acid, DNA) to detect the presence of pre-known mutations, especially single nucleotide polymorphisms (SNPs), using mass spectrometry with ionization by matrix-assisted laser desorption (MALDI).

PRIOR ART

Subject of the invention is a method for the identification of mutations within a certain sequence of the genomic DNA of an organism, either for single mutations or for several mutations simultaneously. These mutative changes of the DNA sequence may be base exchanges ("point mutations", often called SNP="single nucleotide polymorphisms"), the introduction of bases ("insertions"), loss of bases ("deletions") or even changes in the chemical nature of a base by, for example, methylation.

In order to characterize mutations clearly, a DNA sequence in which a mutation is supposed to have taken place must be sequenced from the beginning. In order to find an identified mutation in another individual, resequencing the corresponding DNA section is the best defined form of analysis available. In practice, this would mean that the identification of a known mutation in a subject would cost the same as the original characterization. Different forms of gel electrophoreses are used for the sequencing, but these are slow, expensive and not fully automated.

For this reason, alternative methods were developed for the identification of known mutations. For example, for the identification of many known mutations simultaneously, corresponding DNA sequences could be collected by fixing them onto the surface of a DNA chip. Their hybridization or nonhybridization with added genetic material can be used for the simultaneous identification of various different mutations. Thus, chips with 64,000 fixed sequences have become known. This DNA chip technology, however, has a few significant disadvantages, the most important being the high cost of making the DNA chips. Because determination of a huge number of mutations of an individual is not always necessary, this is not exactly an economic diagnostic method for a certain defined disease.

There is still a need for a method for the rapid recognition of mutations where a moderate degree of multiplex capability would be desirable yet would not be absolutely necessary, if the speed of the individual process is high.

Mass spectrometry using matrix-assisted laser desorption and ionization (MALDI) is a very powerful tool for analyzing biomolecules. The ions can be analyzed for their masses spectrometrically, for example, in a time-of-flight mass spectrometer. Because the speed of flight of the ions is about $10^7$ times faster in the mass spectrometer than the speed of migration of the molecules in the electrophoretic gel, the mass-spectrometric method is extremely fast in comparison to the electrophoretic method, even when measurement of the spectrum is repeated 10 to 100 times to achieve a good signal-to-noise ratio.

The whole MALDI preparation and measurement procedure consists first of embedding the analyte molecules on a sample carrier in a solid, UV-absorbent matrix which is usually an organic acid. The sample carrier is placed in the ion source of a mass spectrometer. The matrix is vaporized by a short laser pulse of around 3 nanoseconds and the analyte molecule is thereby transported into the gas phase in a nonfragmented state. The analyte molecule is ionized by colliding and reacting with the matrix ions generated at the same time. A voltage is applied which accelerates the ions in a field-free flight tube. Due to their different masses, the ions in the ion source are accelerated to different speeds— the smaller ions reaching the detector earlier than the larger ions. The time of flight is converted into the mass of the ions.

Technical innovations in the hardware have significantly improved the time-of-flight mass-spectroscopic method using MALDI. The delayed acceleration (or extraction) method of MALDI ions improves the signal resolution in one place on the spectrum (e.g. U.S. Pat. No. 5,510,613). By subjecting the acceleration voltage to additional dynamic changes, good resolution can be achieved within a wide range of measurement (DE 196 38 577).

MALDI is particularly suitable for the analysis of peptides and proteins; the analysis of nucleic acids is somewhat more difficult. For nucleic acids, the ionization yield in the MALDI process is approximately 100 times less than for peptides and decreases strongly with increasing mass. For the ionization of peptides and proteins, only a single proton needs to be captured. For nucleic acids, which carry many negative charges on their backbone, all these negative charges have to be neutralized, before a further proton creates a positive ion; the ionization by the matrix is therefore significantly less efficient.

For MALDI, the choice of matrix is important. For the desorption of peptides, there are many very efficient matrices. A few effective matrices have been discovered for DNA in the meantime but the extremely low sensitivity compared to proteins was not improved.

The low sensitivity for DNA can be improved by chemically modifying the DNA so that it resembles a peptide. As explained in WO96/2781, phosphorothioate nucleic acids, for example, for which the usual phosphates on the backbone are substituted with thiophosphates, can be converted to a neutral DNA through simple alkylation chemistry, and the chemical covalent bonding of a single positively or negatively charged chemical group ("charge tag") to this modified DNA increases the sensitivity so that it is within the range found for peptides.

These modifications have made it possible to utilize similar matrices to those used for the desorption of peptides. Another advantage of "charge tagging" is the increased independence of the analysis upon impurities which significantly interfere with the identification of unmodified DNA analysis samples.

A new method of mutation diagnostics using MALDI mass spectrometry has recently become known (Little, D. P., Braun, A., Darnhofer-Demar, B., Frilling, A., Li, Y., McIver, R. T. and Köster, H: Detection of RET proto-oncogene codon 634 mutations using mass spectrometry. J. Mol. Med. 75, 745–750, 1997). The primer (a DNA chain which functions as an identification sequence) is synthesized so that it will attach itself near to a known point mutation on the template strand by hybridization. Between the position of this point mutation and the 3' end of the primer (this end is elongated by a polymerase), the sequence of the template strand may consist of a maximum of three of the four nucleo-bases only. At the position of the point mutation, the fourth base appears for the first time. Using polymerase and a particular set of deoxynucleotide triphosphates (which complement the three nucleo-bases which occur between primer and point mutation) and a didesoxynucleotide triphosphate (which is complementary to the potential point mutation) the primer is elongated (or "extended") by duplication. The didesoxynucleoside triphosphate terminates the chain elongation by the polymerase reaction. Depending on whether the point mutation is present or absent, the polymerase reaction is either terminated at the point mutation position or at the next appropriate base adjacent to the potential mutation site. This process (WO 96/29 431, claim 47), which includes attachment of the primer to the surface, has been designated as "PROBE" assay by the authors.

Because unmodified DNA was used for the analysis during this work, a significant disadvantage with this method seemed to be that a relatively large amount of enzymatically generated DNA material had to be made in order to produce signals that could be detected in the analysis which followed. In addition to this, the PCR product had to be immobilized in a solid phase so that the primer, the template strand and the salts and the detergents from the polymerase reaction which would greatly affect the final analysis, can be washed away.

OBJECTIVE OF THE INVENTION

The objective of the invention is to find an improved and simple method of rapid and economic sample preparation for mass spectrometric examination of genetic material for a limited number of known mutations such as base exchanges (point mutations), base additions (insertions), base eliminations (deletions) or even chemical alteration of a base. The DNA chain products should be as short as possible to obtain a precise mass determination, they should be selectively ionized, without washing and cleaning, over all the residual products in the remaining reaction fluid. It should be possible to select the length of the DNA chain products within a certain range so that several mutations could be identified during a single measurement procedure simultaneously.

SUMMARY OF THE INVENTION

Instead of the primers and nucleosides normally used for the PCR, the invention is based on working, during the procedure for primer extension, with fixed positive or negative charge tags on primers or terminating NTPs, and with modified nucleoside triphosphates which, in combination with a later chemical transformation, have the effect of highly increasing the ionization efficiency for the DNA products to be analysed in the MALDI process, as known from WO96/2781.

However, the inventive process removes additionally at least a part of the primer used for the extension process which carries no useful information so that the resulting products are very short, favorable for MALDI mass measurements and sensitivity. Furthermore, the process of the invention uses special MALDI matrix materials which suppress the ionization of residual constituents of the reaction fluid used for primer extension, so that the DNA products do not need any further purification.

The removal of the primer or at least, a part of the primer, can be achieved in various ways:

1. By using normal, unmodified primers which can be removed from the extension product by chemical or enzymatic digestion, e.g., by a phosphodiesterase, which stops at the beginning of the modified bases. In this case, the charge tag has to be on one of ther terminating nucleotide triphosphates.
2. By using a primer with a built-in functional group which can be later activated to cleave the primer.
3. By using modified primers, consisting at the 3'-end out of modified nucleobases and carrying additionally a positive or negative charge tag. The non-modified bases of the primer can be chemically or enzymatically digested.

Removing a part of the primer after extension significantly reduces the mass of the product bringing it to within a mass range where the resolution and precision of the mass determination are considerably improved. According to the current state of technology, isotopic resolution can be achieved within a mass range of 1,500–2,500 Da even in linear time-of-flight mass spectrometers. The high sensitivity in the MALDI process allows to reduce the number of spectrum acquisitions per sample, thus increasing analysis throughput.

Neutralization and charge-tagging allows for non-protonating matrix materials like e.g. α-cyanocinnamic acid methyl ester (α-CNME) for the MALDI process, supressing the ionization of impurities in the sample making purification of the extension product no longer necessary.

Thus, the objective of the invention is achieved. Extension products can be, without further purification steps, ionized during the MALDI process with high sensitivity, selectively and in preference to the other components of the primer extension reaction fluid. The the chain product to be measured can be made as short as possible by completely or partly removing the primer, which offers no information about the mutation, thus decreasing the molecular weight of the DNA chain product and increasing the precision of the mass determination.

In a mixture of all 5 wild types and mutants, 10 different masses were detected after the appropriate work up. In the case of each individual, either the mass of the wild type or the mass of the mutants was found for each system and the distribution of masses was characteristic.

Figure 1:
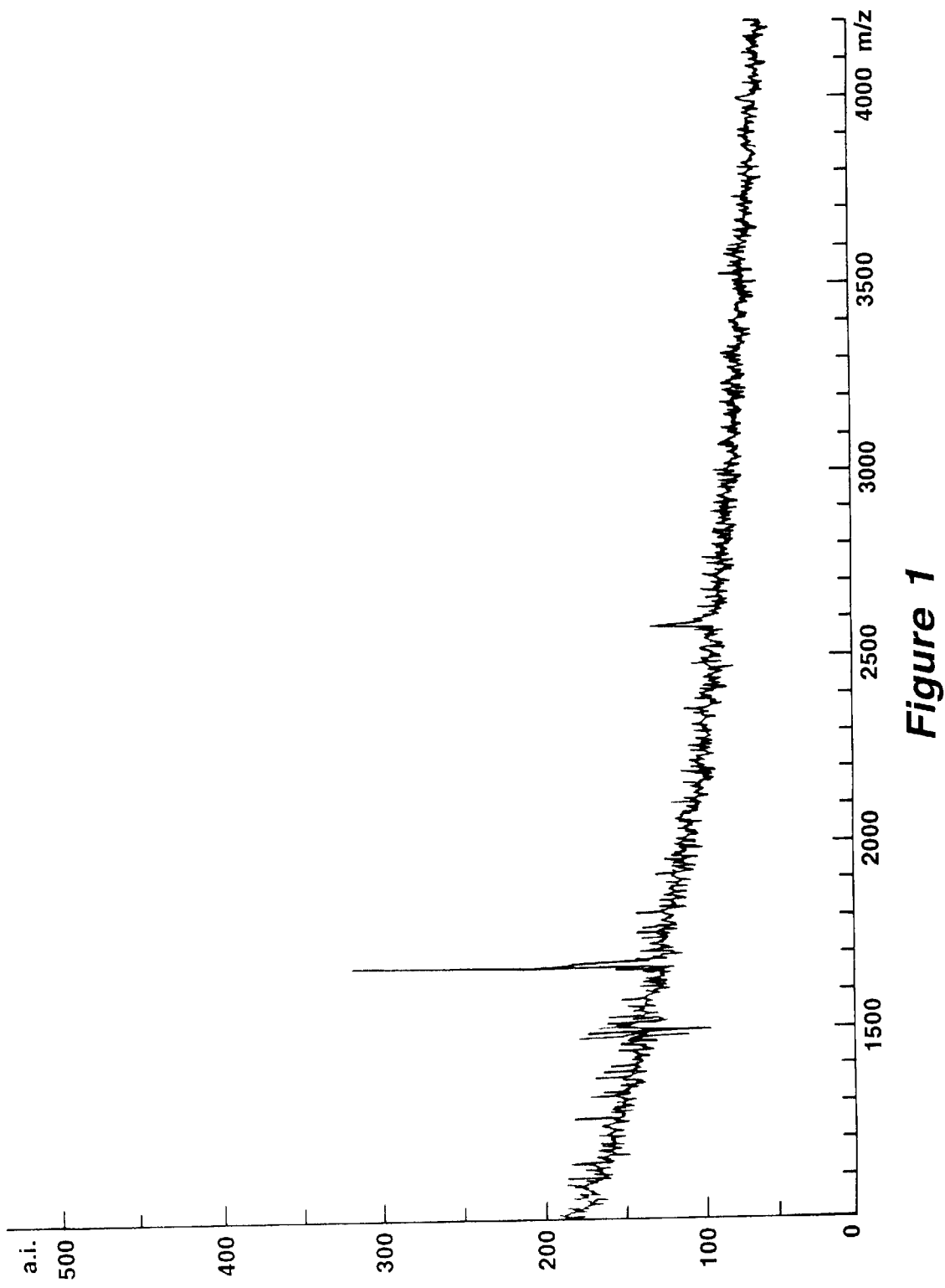
FIG. 1 shows a MALDI mass spectrum with a wild type (homozygote) present. The mass of the wild-type product is 2594 Da. A thin-layer preparation on α-CN-4-hydroxycinnamic acid methyl ester (α-CNME) was used as the matrix.
Figure 2:
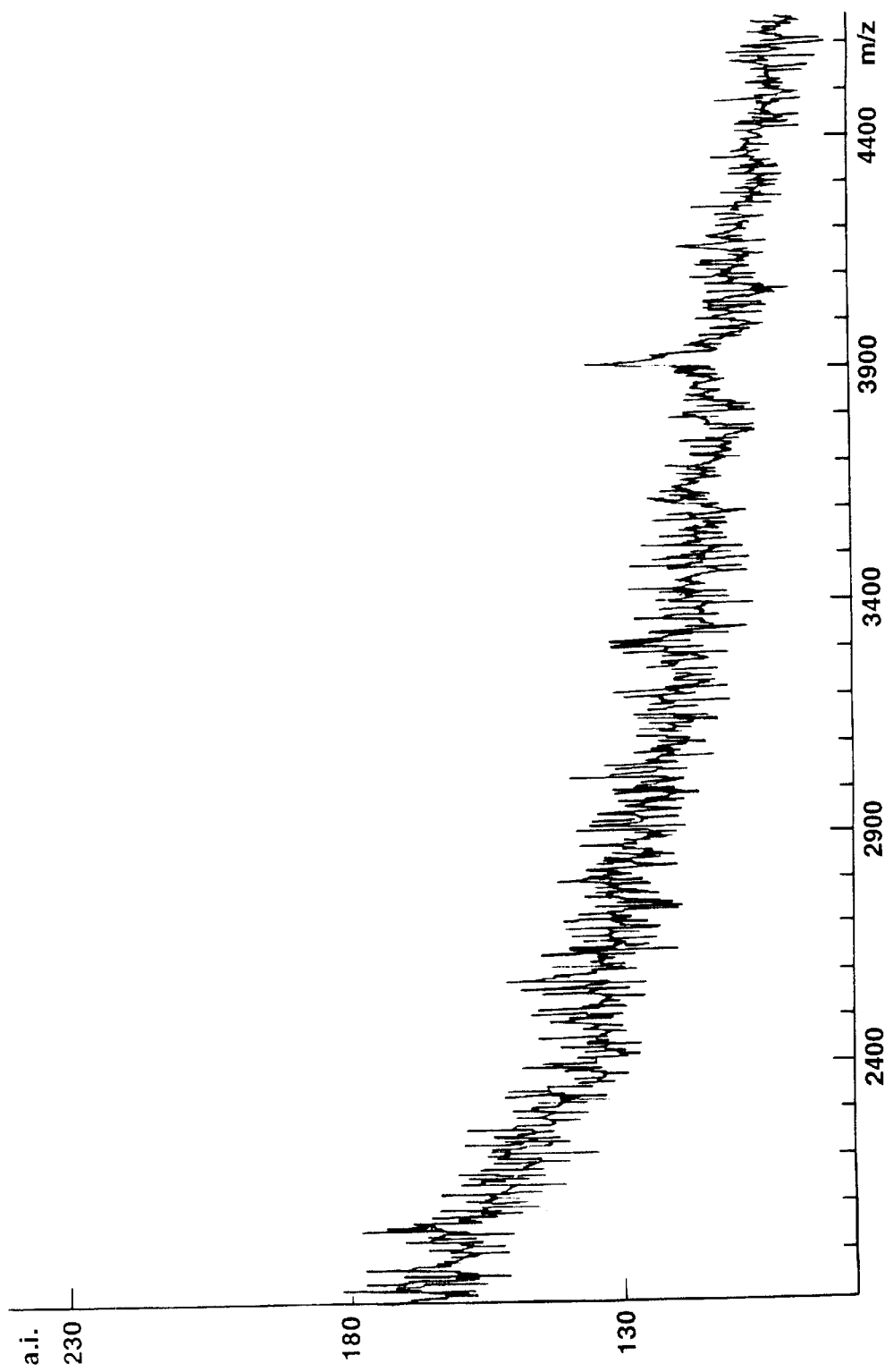
FIG. 2 shows a MALDI mass spectrum with a mutant (homozygote) present. The mass of the mutant product is 3924 Da. A thin-layer preparation on α-CNME was used as the matrix.
Figure 3:
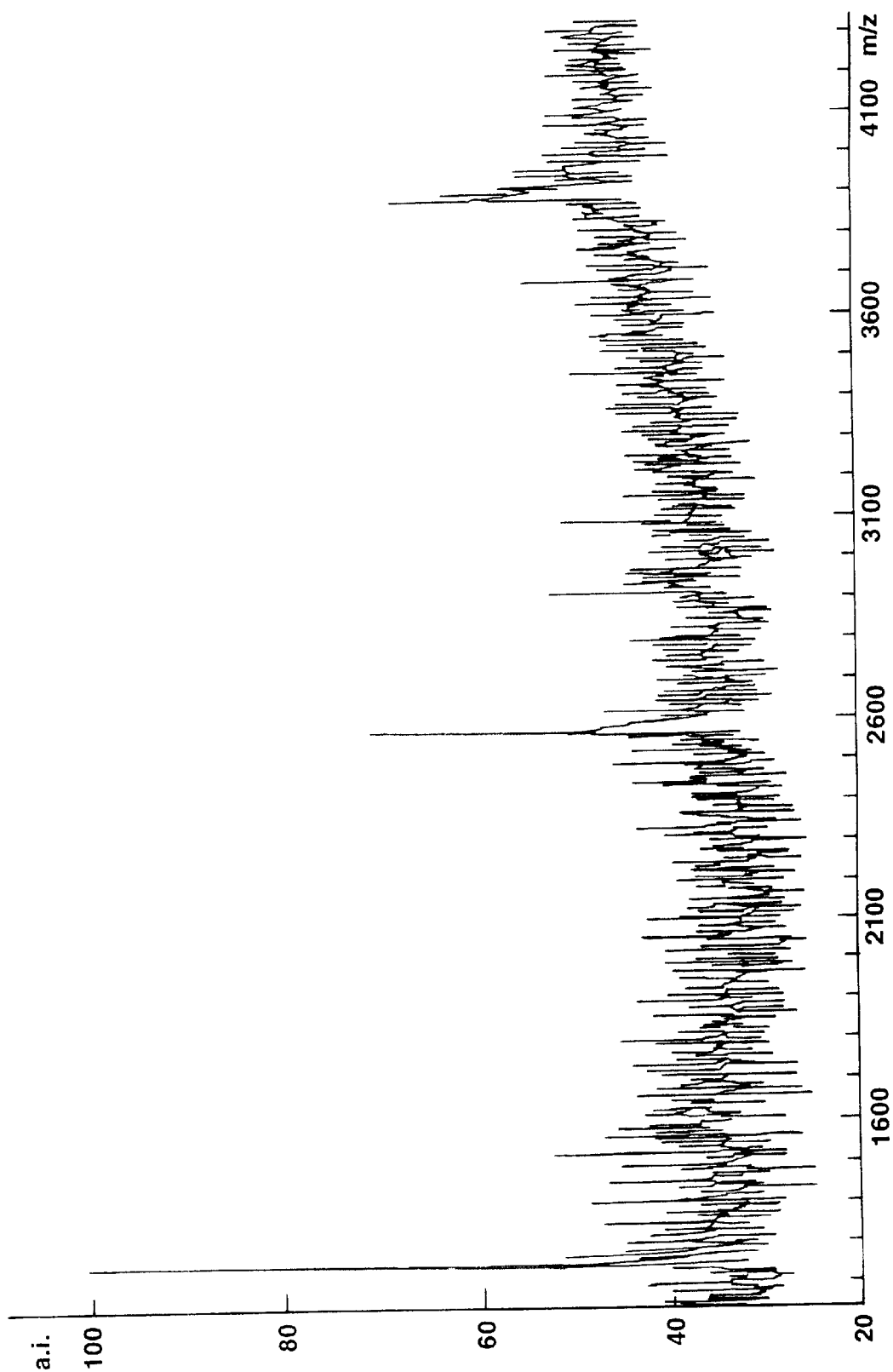
FIG. 3 shows a MALDI mass spectrum with a wild type and a mutant (heterozygote) present. The mass of the wild-type product is 2593 Da and the mass of the mutant product is 3916 Da. The products were made in a duplication reaction with two different templates and appropriately purified simultaneously. A thin-layer preparation on α-CNME was used as the matrix.
Figure 4:
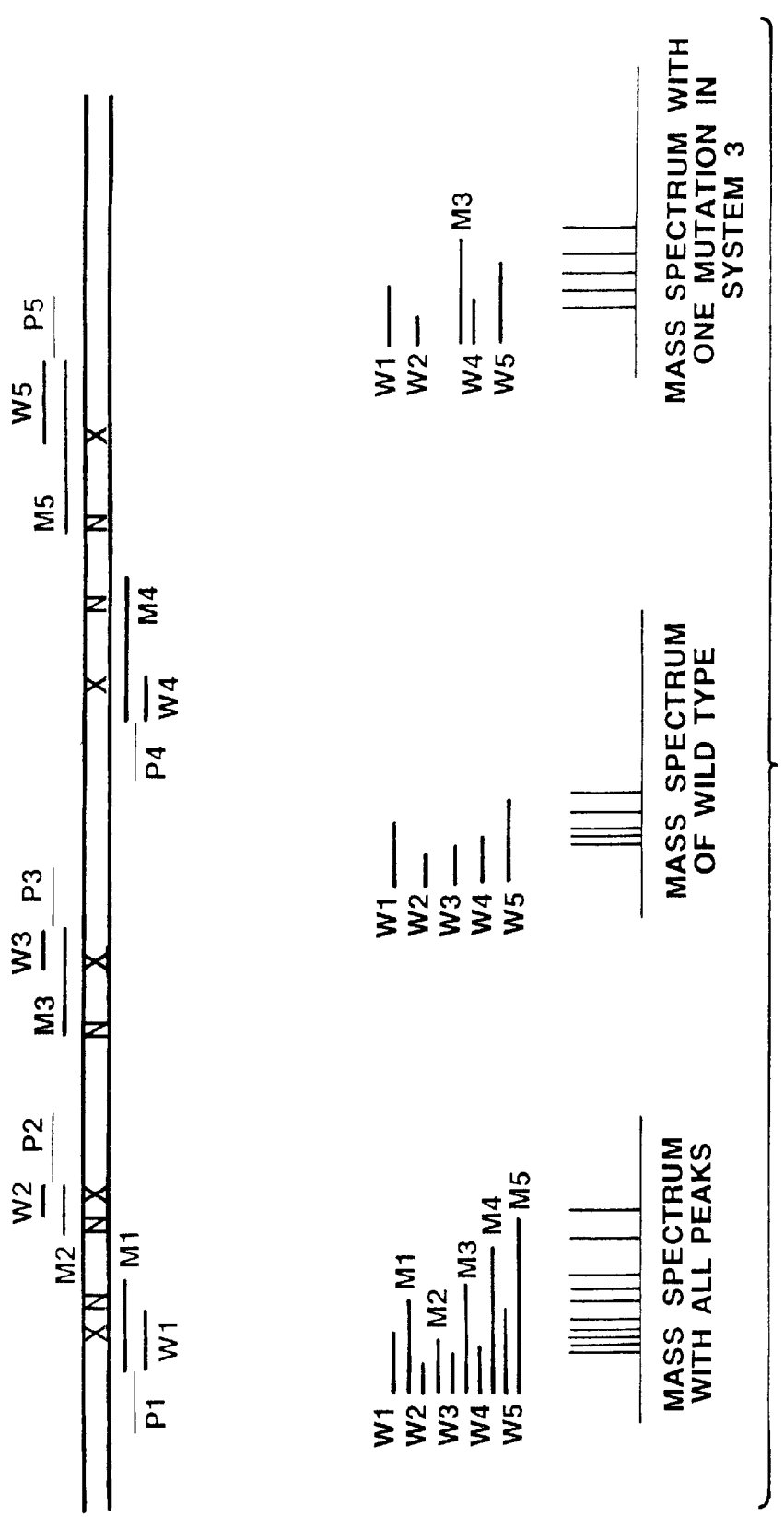
FIG. 4 is a multiplexed scan of a system with 5 potential point mutations according to the principle of the invention. X=the position of the termination in the case of the wild type. N=the position of the termination for an available point mutation.
Figure 5:
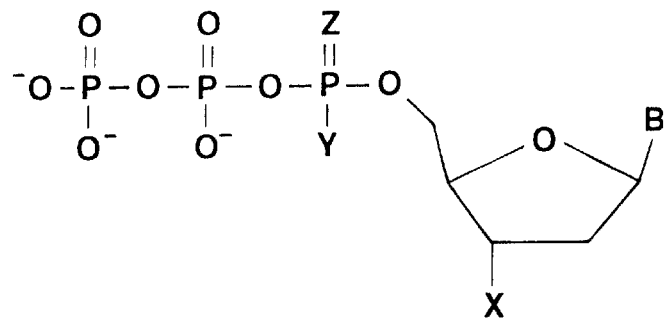

FIG. 5 is a schematic presentation of the nucleotides which may be used in the procedure in question:

X=H, OH, SH, $CH_3$, alkyl, F, Cl, Br, $CT^+$, $CT^-$. X is the functional group which determines whether further polymerization from this position is possible: X=OH facilitates bonding to the next nucleotide while every other functional group prevents it. It is also possible to achieve a shift in the mass by this group.

Y=H, OH, $O^-$, SH, $S^-$, SeH, $Se^-$, $CH_3$, $CH_2F$, $CHF_2$, $CF_3$, alkyl $BH_2$. Y is the functional group responsible for the charge-neutralizing capacity of the microbiologically prepared product, as the α-phosphate group is obtained during polymerization by means of a DNA polymerase, while the β- and γ-phosphate groups are separated. It is also possible to attach the necessary charge tag at this Y position to improve sensitivity during mass-spectrometric analysis (e.g. $CT^+$or $CT^-$).

B=adenine, guanine, cytosine, thymidine, uracil, inosine, purine, pyrimidine, pyrrole, nitropyrrole, indole, nitroindole, deazaguanine, deazaadenine, fluorouracil, bromouracil, pyrazole, imidazole are the usual bases and their substituted derivatives. For B, there are many derivatives of natural nucleo-bases available. The specific base-pairing of the template strand to be duplicated using natural nucleo-bases is essential.

Z=S,O.

product chain in the wild form has a different molecular weight than those of the mutants and, (b) the modification to the nucleoside triphosphates, either alone or in combination with a subsequent chemical treatment (in Step 5), leads to stabilization of the DNA chain during the ionization process and to an adduct reduction of the ions, an increase in the ionization yield and/or a change in the mass of the DNA chain, (3) hybridizing the primer added in Step 2 on a DNA strand and extending the primer by an enzyme which yields a complementary copy of the DNA counterstrand, (4) removing at least a defined part of the primer from the extension product, (5) a further chemical or enzymatic modification of the product chain, leading to extensive neutralization of the DNA (with only one required, preformed charge); and (6) a mass-spectrometric determination of the mass of the modified DNA product chain and assignment of the masses detected to the wild type or known mutants.

The provision of sufficient amounts of DNA in Step (1) may be performed by a polymerase chain reaction (PCR), and subsequent removal of, at least, the remaining nucleotide triphosphates.

The removal can easily be performed using an alkaline phosphatase, e.g., a shrimp alkaline phosphatase (SAP).

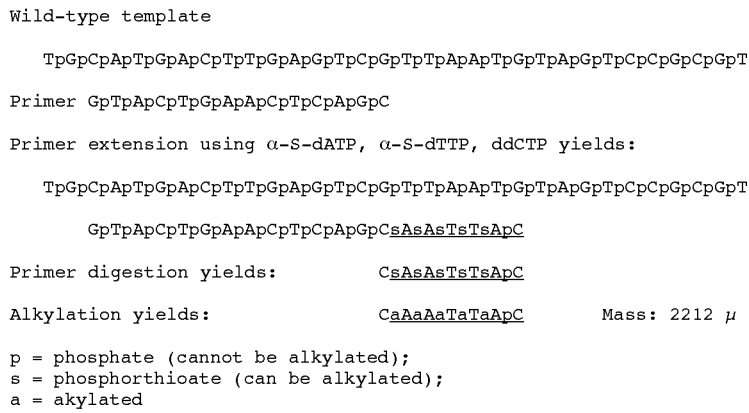

```
Wild-type template

TpGpCpApTpGpApCpTpTpGpApGpTpCpGpTpTpApApTpGpTpApGpTpCpCpGpCpGpT

Primer GpTpApCpTpGpApApCpTpCpApGpC

Primer extension using α-S-dATP, α-S-dTTP, ddCTP yields:

TpGpCpApTpGpApCpTpTpGpApGpTpCpGpTpTpApApTpGpTpApGpTpCpCpGpCpGpT

GpTpApCpTpGpApApCpTpCpApGpCsAsAsTsTsApC

Primer digestion yields:          CsAsAsTsTsApC

Alkylation yields:                CaAaAaTaTaApC        Mass: 2212 μ p = phosphate (cannot be alkylated);
s = phosphorthioate (can be alkylated);
a = akylated
```

Figure 6:
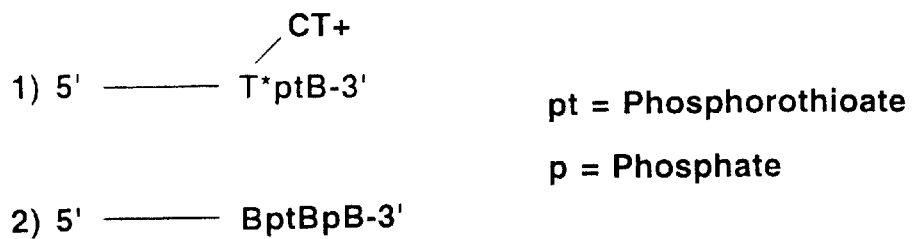
Figure 6:

FIG. 6 shows five primer variants. The nature of primers can be such that they introduce a charge tag into the product. Primer variants 1–3 behave in this way. Alternatively, their composition can be such that they do not contribute any charge to the product, as is the case for Variants 4 and 5. Primers such as these must be combined with a nucleotide system through which a charge tag will be added.

PARTICULARLY FAVORABLE EMBODIMENTS

The procedure used in the invention may consist of the following steps:

(1) providing an amount of DNA containing the mutation,
(2) adding a special set of modified nucleoside triphosphates and a primer, partially consisting of modified nucleobases and carrying a charge tag, for a limited primer extension, where
    (a) the particular set of modified nucleoside triphosphates is assembled so that primer elongation runs as far as or beyond the site of the mutation so that the Diagram 1 is an illustration of the sample preparation for the wild type. A primer is hybridized on a template made using PCR. The primer is extended using a substrate mixture of α-S-dATP, α-S-dTTP and ddCTP, a DNA polymerase and appropriate buffers. Primer extension takes place up to the first G on the template strand and is terminated there by the attached ddCTP. Next, a portion of the product is digested away using a phosphodiesterase. The phosphodiesterase is stopped by the first thiolink to produce a fragment containing only the DNA which has just been made. The product is extensively neutralized by the methylation (e.g. by iodomethane) which takes place next. Using an unmodified phosphate-ddCTP which cannot be alkylated, ensures that a single negative charge is placed on the product, and guarantees its easy ionization to a negatively charged ion.

```
Mutant template:

TpGpCpApTpGpApCpTpTpGpApGpTpCpGpTpTpApApTpApTpApGpTpCpCpGpCpGpT

Primer GpTpApCpTpGpApApCpTpCpApGpC

Chain elongation using α-S-dATP, α-S-dTTP, ddCTP yields:

TpGpCpApTpGpApCpTpTpGpApGpTpCpGpTpTpApApTpApTpApGpTpCpCpGpCpGpT

GpTpApCpTpGpApApCpTpCpApGpCsAsAsTsTsAsTsAsTpC

Digestion yields:          CsAsAsTsTsAsTsAsTpC

Alkylation yields:         CaAaAaTaTaAaTaAaTpC   Mass: 3223 µ

(instead of 2212 µ)
```

Diagram 2 shows the effect of the same sample-preparation procedure for the mutant, the template carrying a point mutation of G to A. The duplication reaction passes the termination site for the wild type and does not stop until it reaches the next G, thus making the mass of the product significantly larger.

A procedure which is particularly preferred therefore will appear as follows: For the initial PCR multiplication for providing sufficient DNA for Step 1, the primers naturally must be selected so that the known point mutations, insertions and deletions which are to be examined are in the PCR product produced. It is necessary to remove the PCR-amplification residue nucleoside by generally known procedures, e.g. by using a "nucleotide removal kit" produced by QIAGEN. Alternatively, the residual nucleotides can be mixed with an alkaline phosphatase and the solution processed without further purification.

In Step 2, a reduced set of modified desoxynucleotide triphosphates (e.g. α-S nucleotides or α-methyl nucleotides) is added in which the one type of nucleotide is missing, at which chain elongation should stop. This end must be selected so that the molecular weight of the product chain gives information about the type of mutation. Alternatively, a terminating didesoxynucleo triphosphate may be added which is not present as a desoxynucleo triphosphate. This will ensure that specific chain termination products are formed during Step 3, as shown in the above Diagrams 1 and 2.

Modified nucleotides are used here as base for the invention. Thus, using neutralized nucleotides, such as α-methyl nucleotides for example, the polymerase reaction can produce a neutrally charged DNA backbone. α-S nucleotides can easily be neutralized in Step (4) after being integrated into the DNA chain, for example, by alkylation and methylation in particular.

Apart from this, new primers are added during Step 2 which are able to bond closely enough to the mutation sites for a chain termination to give information about the mutation as is known from the usual primer extension procedures like, e.g., PROBE. It is advisable that the primers already carry the charge tags for positive charge tagging. It is advantageous for the charge tag to be attached near to the 3' end of the primer but not on the end base itself. The nucleobases at the 3' end of the primer should be modified so that, on the one hand, they can be charge neutralized or are neutrally charged already and, on the other hand, they are able to resist the later removal of part of the primer.

During Step 3, the primers added in Step 2 are now attached to one strand of the DNA provided in Step 1 and then elongated by enzymatic duplication. Neither the primers nor the DNA strands need to be immobilized on a fixed surface, unlike the situation found in the work of Little et al. mentioned above.

During Step 4, the DNA chain products are shortened by selectively removing the sequences originating from the primer. The chemical and enzymatic reactions, which are preferably used here, are the removal of the primer or significant parts of the primer from the chain products after the polymerase reaction, for example, by a 5' phosphodiesterase or by activating a chemical cleavage function integrated in the primer. As the primer contains no new information and would only interfere during the mass-spectrometric analysis, it is advisable to remove it.

In Step 5, the chemical treatment takes place which leads to neutralized products provided with a charge tag. These are particularly easy to ionize by MALDI. Preferably, the chain products will be neutralized by an alkylation reaction if, for example, α-S nucleotides have been used for the duplication reaction.

The mass-spectrometric measurement of the DNA-chain-product masses carried out by MALDI during Step 6 in a suitable mass spectrometer, such as a time-of-flight mass spectrometer, using this form of sample preparation, in principle corresponds to the prior art. Assignment of the masses to the type of mutation or wild type also corresponds to the prior art.

The kind of matrix material used in the MALDI process, however, can be quite different. Because the primer extension products produced here already carry a charge tag, they do not need to be ionized by the matrix ions. Thus non-protonizing matrix materials may be used suppressing ionization of the other constituents of the MALDI preparation, allowing the unpurified extension product to be measured. After adding some suitable matrix material to the neutralized extension products obtained in Step (5), droplets of the liquid may be transferred to the sample carrier without further cleaning. Usually matrix materials consist of organic acids for good protonation, here, in contrast, esters of these acids may be used, for example α-cyanocinnamic acid methyl ester.

A very important point is the use of charge tags, which significantly increases the detection capability of the products. Here, there are several variants available: 1) integration of a positive charge tag in the primer (for example, via T*). 2) Integration of a negative charge tag in the primer (for example, via an unmodified phosphate link). 3) Integration of a positive charge tag by the terminator (such as an α-S 3' CT didesoxynucleotide). 4) Introduction of a negative charge tag by an unmodified didesoxynucleotide triphosphate which cannot be alkylated.

Using a charge tag is, of course, only advisable in combination with the removal of all other remaining charges from the DNA products as, only under these circumstances, will the charge state of the analyte molecule be completely defined. By attaching a charge tag and neutralizing the charge of the remaining DNA, the sensitivity will be improved 100 times and matrices can be used which selectively support desorption of these modifications, so that the mass spectrometric analysis can be carried out without purification.

DNA has a polyanionic backbone. By replacing phosphate links in the DNA backbone with phosphorothioate links, a chemical function is produced in which the negative charge can be removed using simple chemical techniques. Alternatively, modified nucleotides, such as $\alpha$-methyltriphosphate nucleotides, can be used from the outset which, after their polymerization, lead to charge neutrality on the DNA backbone. At the same time, neutralizing the DNA not only contributes to raising the ionization yield but also suppresses the formation of adducts and helps to stabilize the DNA during the MALDI process.

On the one hand, this method has the potential to increase sensitivity and diminish the formation of adducts by the implemented modifications and, on the other hand, certain classes of substance can be selectively suppressed from ionization during MALDI spectrometric procedure, thus fading out undesirable reaction side products.

In practice, this means that, by means of the modifications introduced and the mass-spectro-metric parameters selected, the relevant products can be analyzed exclusively. For instance, the template DNA can be faded out completely and does not, therefore, have to be removed during a purification step. This also increases the possibilities in regard to multiplexing. The whole process can be carried out without any or with very little purification after the enzymatic and chemical reaction steps.

The important variants of the method are summarized in FIGS. 5 and 6. In principle, each nucleotide variant can be combined with each primer variant (for chain elongation nucleotides, X=OH, thus, a termination nucleotide is characterized by the fact that X≠ OH). However, there are combinations which are less sensible. Useful variants carry the charge tag (abbreviated to "CT" in FIGS. 5 and 6) either on the primer or on the terminator. Sensible variants which receive the charge tag included with the terminator are used in combination with primers without a charge tag. A charge tag on the terminator adds a charge to the product chain via $X=CT^+$ or $CT^-$, Y=OH or $O^-$. In one variant in which chain elongation nucleotides are neutrally charged without subsequent chemical modification (Y=$CH_3$, $CH_2F$, $CHF_2$ or $CF_3$), a charge can also be introduced in the terminator nucleotide with X or Y=SH, $S^-$, SeH or $Se^-$.

Only those modifications which contain neutrally charged or Y link groups which can be neutralized are used as chain-elongation nucleotides, i.e. Y itself must be neutrally charged (Y=H, $CH_3$, $CH_2F$, $CHF_2$, $CF_3$ or alkyl) or be able to be neutralized quantitatively (Y=SH, $S^-$, SeH, $Se^-$). Primers 1 to 3 are used in systems in which all chain-elongation nucleotides and terminators can be neutralized or carry neutral link groups. B must be introduced as defined and complementary to a base.

An increase in sensitivity compared to conventional DNA can be achieved to a small degree if no charge tag is used and only the backbone of the analyte is completely neutralized. In this case, however, a MALDI matrix must be used which is able to protonate the analyte. Here, $\alpha$-cyanocinnamic acid and sinapic acid can be used as matrices and have already proven themselves for peptides. The DNA-specific problem of the polyanion, which must be transferred by means of a matrix into a singly charged species with correspondingly minimal efficiency, is essentially obviated even when the backbone alone is neutralized. The advantage of the variant is that there are several MALDI matrices available which have already been tried and tested on other classes of substances.

Unmodified oligonucleotides or DNA itself are not very suitable, as their capacity for detection via, for example, MALDI or ESI mass spectrometry is limited. Another advantage offered by our invention is that preferential extraction can be achieved during the mass-spectrometric analysis because of the exclusive introduction of chemical modifications into the newly generated DNA fragments. For this, there are available modifications such as alkylated phosphorthioate DNA or methylphosphonates coupled with charge tags. The capacity for detection of this modified DNA using mass spectrometry is 100 times greater than that of the unmodified sequences.

An example of a typical mutation analysis is given in the above Diagrams 1 and 2. This analytical procedure utilizes a primer which can be separated by chemical means or by means of an enzyme after the polymerase reaction together with a set of $\alpha$-S-dNTPs (for example, for the bases C, G and A) and a ddNTP (in our example for the base T). Using a polymerase, the chain is lengthened on a template with a possible point mutation which, in this example, yields an elongation of 9 bases for the mutation type and 6 bases for the wild type without mutation. After this, the portion of the product stemming from the primer is removed using an enzyme or by chemical means and the product alkylated. All thioate links may be alkylated except the standard phosphate links introduced via the terminator. This charge functions as a negative charge tag. In the negative-ion mode of the mass spectrometer, the products with a termination can now be identified in high yield and, therefore, almost exclusively (as a 10 member or 7 member chain). These are easily distinguished by their masses and a direct statement can be made on the existence of a point mutation. Furthermore, because of the increase in sensitivity resulting from the modifications described, significantly less material needs to be prepared and measurement of the modified product is also considerably less sensitive to impurities from the polymerase storage buffers and PCR buffers. We are, therefore, able to operate without purification and carry out the polymerase reaction, the separation of the primer and the alkylation consecutively and then detect acceptable signals during the MALDI analysis.

One variant would be to use a terminator into which a quarternary amino function has been synthesized. This component must be prepared in the $\alpha$-S variant. We have already carried out and established the synthesis of this component. An analysis could, therefore, be carried out in positive-ion mode.

By using an appropriate design for the primers, cleavage functions and different distances to the point-mutation positions, familiar to every specialist working in this area, it is also possible to analyze several point-mutation systems simultaneously (multiplex). Indeed, these could be analyzed on both DNA strands of the DNA double strand, i.e. in opposing directions.

Not only can the analysis of a single PCR product be carried out in multiples but also a single multiplex analysis can be carried out at the same time using a segment of several PCR products duplicated in a single multiplex PCR procedure. Thus, different parts of a genome are amplified in a multiplexed PCR simultaneously. Next, the analysis can be carried out on each PCR product with the necessary number of primers. What is important is that all individual analyses are carried out with the same combination of nucleotides and this fact must be taken into account while planning and preparing the multiplex system. In principle, any information wanted about the mutations in a genomic DNA can be scanned using a combination of a maximum of four nucleotide systems.

Even using all four α-S-dNTPs and one ddNTP is possible, whereby a sequence ladder is produced. It is also possible to mix, for example, a positive CT terminator from one base and a negative CT terminator from a second base in a single sequence reaction. The termination via one base can then be analyzed in positive-ion mode and the termination via the other base analyzed in negative-ion mode.

The detection response in the MALDI mass spectrometer decreases with the increasing mass of the analyte molecule. It is therefore advisable to remove sequences without informative content before carrying out the MALDI analysis. This applies, above all, to the primer used for the duplication reaction, the sequence of which must inevitably be already known and will therefore contain no new information.

We have developed two procedures for this purpose. In one case, the cleavage may be carried out at a thioate link through alkylation using a hydroxyalkiodide. Next, basic cleavage can be performed selectively at this position on the backbone (several hydroxyalkiodides have been tested for this purpose).

Another possibility is the enzymatic digestion of the unmodified primer starting from the 5' end. Using 5' phosphodiesterase, a portion of the primer will be digested up to a phosphorothioate function in the vicinity of the 3' end of the primer. The interruption of exonuclease digestion caused by the phosphorothioate gives the new 5' end a uniform function. When there is a charge tag on the 3' side of the stop function, exonuclease digestion operates accordingly.

Immediately after the product-DNA segments not linked with thioates have been digested, the buffer solution is lyophilized and the thioate links alkylated. For this, the lyophilate is taken up in 10 µl bi-distilled water and mixed with 37.5 µl acetonitrile, 10 µl M triethylammonium hydrogen carbonate buffer and 15 µl iodomethane. The two-phase mixture is incubated at 41° C. for 30–40 minutes (depending on the length of the DNA being analyzed), the solvent distilled away and the residue taken up in 150 µl–600 µl 40% acetonitrile. Next, 0.2 µl of this solution is applied to the MALDI target previously coated with α-cyanocinnamic acid methyl ester (or α-cyanocinnamic acid for analytes without a charge tag) as the matrix and the sample analyzed.

The alkylation method is equally suitable for all variants described with positive or negative fixed charge carriers already preformed in the analyte and for variants for which the bonding of a charge tag is not intended.

If, however, after the portion of the analyte not linked to thioates has been digested, a charge tag is integrated at the same time and neutralization of the DNA polyanion is achieved, then the following variants are also available: 30 µl educt in TE buffer is mixed with 150 µl acetonitrile, 60 µl 2M triethylammonium hydrogen carbonate buffer (pH 8.5), 60 µl of a 1% solution of 6-trimethylammoniumhexnoic acid N-hydroxysuccinimidyl ester in water and 60 µl iodomethane in a 1.5 ml Eppendorf vessel and the two-phase mixture warmed for 45 minutes at 37° C. without shaking. The mixture is lyophilized and taken up in 40% acetonitrile for the MALDI analysis. The feedstock is optimized to the simultaneous charge-tagging and alkylation of larger quantities of material. A primary amino function in the educt is a prerequisite. As a rule, this is introduced via a modified primer.

As an alternative, a stock solution of the charge-tag reagent can be prepared by dissolving 2 mg (4-iodobutyl)-triethylammonium iodide in 2 M triethylammonium hydrogen carbonate buffer (10 µl). Different amounts of this stock solution are used for the following alkylation protocol depending on the length of the oligomer to be alkylated: 2 µl of the educt solution in water (approx. 500 pmol/µl), 15 µl DMF, 1 µl iodoethane and 9/n µl of the charge-tag stock solution plus 2–9/n µl 2 M triethylammonium hydrogen carbonate buffer (n=number of bases in the thioate DNA to be alkylated) are incubated at 55° C. for 30 minutes. The solvent is distilled away under vacuum. MALDI mass-spectrometric analysis shows that, under these conditions, approximately 30% of the required product with a single fixed charge is formed. This can also be detected selectively using an non-acidic matrix such as α-cyanocinnamic acid methyl ester.

A recipe for the synthesis of (4-iodobutyl)-triethylammonium iodide as the backbone chargetag reagent should be added here: a solution of 1 ml (5 mmol) 1,4-diiodobutane in 5 ml nitromethane is mixed drop-wise at room temperature with 0.6 ml (4.5 mmol) triethylamine. The solution is heated under reflux for 1 hour, cooled and concentrated under vacuum. The oily residue is washed with three 2 ml portions of n-heptane. After evaporating the solvent under vacuum, a yellow solid is obtained which is washed first with n-heptane, then with diethylether and finally dried under high vacuum.

The recipe for making a primer with a charge on the thymine base is as follows: The commercially synthesized primer with a free primary amino function on a thymine base is dissolved in a TE buffer and adjusted to a concentration of around 500 pmol/µl. 30 µl of this solution is mixed with 1.5 µl of a 2 M triethylammonium hydrogen carbonate solution (pH=7.5) and at 0° C. with 24 µl of a freshly prepared 1% solution of 6-trimethylammoniumhexanoic acid N-hydroxysuccinimidyl ester in bi-distilled water. After 30 minutes at 0° C., the solution is concentrated to dryness under vacuum. The residue is taken up in 15 µl 300 mM ammonium acetate solution and the DNA is precipitated by the addition of 60 µl ethanol. Precipitation is completed by standing the mixture at 20° C. for 2 hours and the precipitate separated out by centrifugation. The supernatant is removed and the pellet rinsed with two 50 µl portions of 80% ethanol and dried under vacuum.

Recipe for the synthesis of a terminator provided with a charge tag: 3'-amino-3'-desoxy-thymidine (50 mg, 207 µmol) is dissolved in 1 ml bi-distilled water and mixed with 50 µl 2 M triethylammonium hydrogen carbonate buffer. Then, 60 mg (210 µmol) 6-trimethylammonium-hexanoic acid N-hydroxysuccininidyl ester is added as a solid under rapid stirring at 0° C. Stirring is continued for a further 60 minutes at 0° C. and the solvent removed under vacuum. The residue is washed with dichloromethane and taken up into water. During lyophilisation, a white foam is produced. The raw charge-tag nucleoside is transferred to the corresponding 5'-α-S-triphosphate according to a method published in the literature (Ludwig, J. and Eckstein, F. "Rapid and efficient synthesis of nucleotide 5'O-(1-thiotriphosphates), 5' triphosphates and 2',3'cyclophosphorothioates using 2-chloro-4H- 1,3,2-benzodioxaphosphorine-4-one". J. Org. Chem. 54, 631–635, 1989) and, not until this stage, purified by ion-exchange chromatography on DEAE Sephadex A-25.

EXAMPLES (1) Using a thioate terminator with a positive charge tag:
Base sequence of wild type:
5'-TCC TGC ATG GGC GGC ATG AAC CGG AGG CCC ATC-3' (SEQ ID NO:1)
Base sequence of mutant:
5'-TCC TGC ATG GGC GGC ATG AAC CGG AGT CCC ATC-3' (SEQ ID NO:2)
The following are used as the nucleotides in the duplication reaction: dGTP-αS, dATP-αS, dCTP-αS, ddt$^{ct}$TP-αS
Primer (complement): 5'-C TGC ATG GGC GGC ATG AAC CG-3' (SEQ ID NO:3). Backbone, standard phosphates
Product when there is a wild type present after nuclease digestion and alkylation:
5'-GaAaGaGaCaCaCaAaT$^{ct}$, m/z=3116
Product when there is a mutant present after nuclease digestion and alkylation:
5'-GaAaGaT$^{ct}$, m/z=1457

(2) Using an unmodified dideoxy terminator (negative charge tag):
Base sequence of wild type:
5'-AGC TAC TGA TGC TGT GCA GAC ACT T-3' (SEQ ID NO:4)
Base sequence of mutant:
5'-AGC TAC TGA TGC TGT GCA GAC ACT T-3' (SEQ ID NO:5)
The following are used as the nucleotides in the duplication reaction: dGTP-αS, dATP-αS, dCTP-αS, ddTTP
Primer: 5'-AGC TAC TGA TGC TGT GC-3'(SEQ ID NO:6). Backbone, standard phosphates
Product when there is a wild type present after nuclease digestion and alkylation:
5'-AaGaApT-3', m/z [M$^-$]=1240
The following are used as the nucleotides in the duplication reaction: ddGTP-αS, dATP-αS, dCTP-αS, dTTP-αS
Primer: 5'-GGA ACA GCT TTG AGG sTG-3' (SEQ ID NO:7)
Product when there is a wild type present after nuclease digestion and alkylation:
5'-GaTpGaCaG-3', m/z [M$^-$]=1591
Product when there is a mutant present after nuclease digestion and alkylation:
5'-GaTpGaCaAaTaG-3', m/z [M$^-$]=2268

(6) Using a primer with a negative charge tag without terminator (leaving out a nucleotide):
Base sequence of wild type:
5'-GGA ACA GCT TTG AGG TGC GTG TTT GTG-3' (SEQ ID NO:8)
Base sequence of mutant:
5'-GGA ACA GCT TTG AGG TGC ATG TTT GTG-3' (SEQ ID NO:9)
The following are used as the nucleotides in the duplication reaction: dATP-αS, dCTP-αS, dTTP-αS
Primer: 5'-GGA ACA GCT TTG AGG sTG-3' (SEQ ID NO:10)
Product when there is a wild type present after nuclease digestion and alkylation:
5'-GaTpGaC-3', m/z [M$^-$]=1248
Product when there is a mutant present after nuclease digestion and alkylation:
5'-GaTpGaCaAaT-3', m/z [M$^-$]=1925

(7) Variant without charge tagging using a phosphorothioate terminator:
Base sequence of the wild type;
5'-GCT GAC ATT GAA ATA TGG CGC CAA GCA TGT-3' (SEQ ID NO:11)
Base sequence of the mutant;
5'-GCT GAC ATT GAA ATA TGG CGT CAA GCA TGT-3' (SEQ ID NO:12)
The following are used as the nucleotides in the duplication reaction: ddTTP-αS, dATP-αS, dCTP-αS, dGTP-αS
Primer: 5'-GCT GAC ATT GAA ATA TG-3'(SEQ ID NO:13), standard phosphates on the backbone
Product when there is a wild type present after nuclease digestion and alkylation:
5'-GaCaGaCaCaAaAaGaCaAaT-3', m/z [M$^+$]=3609 (SEQ ID NO: 18)
Product when there is a mutant present after nuclease digestion and alkylation:
5'-GaCaGaT-3', m/z [M$^-$]=1264

(8) Example of a variant without charge tagging and without terminator (leaving out a nucleotide):
Base sequence of the wild type:
5'- ATT GAA ATA TGG CGC CAA GCA TGT GAT-3' (SEQ ID NO:15)
Base sequence of the mutant;
5'- ATT GAA ATA TGG CGC CAA GCA TTT GAT-3' (SEQ ID NO:16)
The following are used as the nucleotides in the duplication reaction: dATP-αS, dCTP-αS, dTTP-αS
Primer: 5'-ATT GAA ATA TGG CGC CAA G-3' (SEQ ID NO:17)
Product when there is a wild type present after nuclease digestion and alkylation:
5'-CaAaT-3', m/z [M$^+$]=905
Product when there is a mutant present after nuclease digestion and alkylation:
5'-CaAaTaTaT-3', m/z [M$^+$]=1573

---

What is claimed is:

1. Method for the mass-spectrometric analysis of a known mutation site in genomic DNA wherein the method is performed without purification or isolation of extended product chains during the course of the mass-spectrometric determination comprising:
   1) providing a DNA segment comprising a genomic sequence including said mutation in site,
   2) adding to the DNA, primers comprising linkages that are susceptible to a digestion procedure to remove at least part of the primers and a set of non-terminating nucleotide triphosphates (NTP) and terminating nucleotide triphosphates which form linkages that are not susceptible to said digestion procedure, wherein at least one of the primers or the set of nucleotide triphosphates includes charge tags,
   3) hybridizing the primers to the DNA and extending the primers in an enzymatic complementary copy reaction, such that product chains are formed where each product chain includes a section complementary to a DNA portion containing the mutation and one of the charge tags,
   4) digesting each of the primers from the extended primer product chains of step 3, such that any of the primer portions no longer attached to the extended product chains are completely degraded, leaving charge tags attached to the remaining extended product chains,
   5) charge neutralizing, if not already neutrally charged, the remaining extended product chains except for the charge tags, and
   6) mass-spectrometrically determining the mass of the product chains wherein the mass of the extended product chain is used to determine the known mutation.

2. Method according to claim 1, wherein in step (1) the DNA is provided by a process that includes PCR.

3. Method according to claim 2, wherein in step (1) the DNA is provided by a process that includes digestion of nucleotide triphosphates by a phosphatase following the PCR.

4. Method according to claim 1, wherein in step (2) the charge tags are bonded to the terminating nucleotide triphosphates, and wherein the primers, in step (4), are removed completely.

5. Method according to claim 4, wherein the primers are digested with 5' phosphodiesterase.

6. Method according to claim 1, wherein the primers added in step (2) for the primer extension carry a chemical group which can be activated, in step (4), to cleave the primer.

7. Method according to claim 1, wherein the primers added in step (2) comprise unmodified nucleobases at the 5'-end, and modified nucleobases at the 3'-end, and wherein only the unmodified parts of the primers are removed in step (4).

8. Method according to claim 7, wherein the unmodified parts of the primers are digested with 5' phosphodiesterase.

9. Method according to claim 7, wherein the primers carry a charge tag at one of the modified nucleobases and the terminating nucleotide triphosphates do not carry a charge tag.

10. Method according to claim 9, wherein the primers carry a charge tag at the second, third or fourth modified nucleobase counted from the 3'-end.

11. Method according to claim 9, wherein the charge tag consists of an ammonium group.

12. Method according to claim 7, wherein the primers carry an anchor for a charge tag which is attached in Step (5).

13. Method according to claim 12, wherein the anchor for the charge tag consists of an amide group.

14. Method according to claim 1, wherein the nucleotide triphosphates added in step (2) carry a negatively charged Sulfur group ($Y=S^-$) in α-position (thiophosphate), and wherein the neutralization in step (5) is performed by alkylation of the Sulfur group.

15. Method according to claim 1, wherein the terminating nucleotide triphosphates added in step (2) are didesoxynucleotide triphosphates.

16. Method according to claim 1, wherein excess product charges are charge-neutralized in step (5) by chemical means.

17. Method according to claim 16, wherein the excess product charges are charge-neutralized in step (5) by alkylation.

18. Method according to claim 1, wherein matrix-assisted laser desorption and ionization (MALDI) is used for ionization in the mass-spectrometric mass determination in step (6).

19. Method according to claim 18, wherein a matrix is used for the MALDI ionization which almost exclusively ionizes, in step (6), the product chains produced in steps (3) to (5).

20. Method according to claim 19, wherein the matrix is α-cyano-4-hydroxycinnamic acid methyl ester.

21. Method according to claim 1, wherein electrospray ionization is used for the ionization in the mass-spectrometric mass determination in step (6).

22. Method according to claim 1, wherein several different segments of DNA are provided in step (1), and, in step (2), several different primers are used at the same time and the resulting products are taken through the steps yielding product chains of various masses.

* * * * *